United States Patent [19]

Sasa et al.

[11] Patent Number: 4,579,597
[45] Date of Patent: * Apr. 1, 1986

[54] METHOD OF CLEANING ENDOSCOPE CHANNELS

[75] Inventors: Hiroyuki Sasa; Hisao Yabe; Yukio Nakajima; Fumiaki Ishii; Koji Takamura; Takeaki Nakamura, all of Tokyo, Japan

[73] Assignee: Olympus Optical Co., Ltd., Tokyo, Japan

[*] Notice: The portion of the term of this patent subsequent to Jun. 25, 2002 has been disclaimed.

[21] Appl. No.: 604,517

[22] Filed: Apr. 27, 1984

[30] Foreign Application Priority Data

May 2, 1983 [JP] Japan .................................. 58-77893
May 16, 1983 [JP] Japan .................................. 58-85553

[51] Int. Cl.$^4$ ............................ B08B 3/04; B08B 9/00
[52] U.S. Cl. .................................. 134/21; 134/22.12; 134/22.18; 134/24; 134/34; 422/33
[58] Field of Search ............... 134/21, 22.12, 22.18, 134/24, 166 C, 169 C, 171, 34; 128/6; 239/106, 112; 422/28, 33

[56] References Cited

U.S. PATENT DOCUMENTS

| | | | |
|---|---|---|---|
| 2,993,494 | 7/1961 | Svensson | 134/169 C |
| 3,963,438 | 6/1976 | Banez | |
| 4,064,886 | 12/1977 | Heckele | 134/171 X |
| 4,216,767 | 8/1980 | Aoshiro | 134/171 X |
| 4,278,101 | 7/1981 | Tanaka et al. | 134/171 X |
| 4,281,646 | 8/1981 | Kinoshita | 128/6 |
| 4,281,674 | 8/1981 | Tanaka et al. | 134/171 X |
| 4,288,882 | 9/1981 | Takeuchi | 134/199 X |
| 4,299,244 | 11/1981 | Hirai | 134/171 X |

Primary Examiner—Marc L. Caroff

[57] ABSTRACT

In a method of cleaning an endoscope, the open ends of an air/liquid supply valve cylinder, a suction valve cylinder, and a gas supply valve cylinder which are arranged in a control section of the endoscope are closed by stops. An air supply channel, a liquid supply channel, a suction channel, and a gas supply channel of the endoscope open at one end to a connector mounted on the distal end of the light guide cable of the endoscope. The connector is submerged in the liquid held in a tank. A cap is mounted on the distal end of the insertion section so that a nozzle communicating with the channels and a suction opening communicating with the suction channel open to the interior of the cap. The cap is connected to a suction pump by a suction tube. The pump is operated, thus sucking the liquid from the nozzle and suction opening through the four channels and the three cylinders, thereby cleaning the interiors of these channels and cylinders.

3 Claims, 3 Drawing Figures

METHOD OF CLEANING ENDOSCOPE CHANNELS

BACKGROUND OF THE INVENTION

The present invention relates to a method of cleaning an endoscope.

An endoscope generally has various channels for supplying or drawing by suction air or liquids. Therefore, when a used endoscope is to be cleaned, not only the outer surface thereof but also the channel interiors must be cleaned. The word "cleaning" used herein includes the steps of cleaning the channels with water to remove contaminants from the channels, then disinfecting them with a disinfectant, and again washing them with water. However, in a conventional method of cleaning the channel interiors, a cleaning solution injection tube must be inserted in the port of each channel, and the valve of each channel must be opened. This requires connection of the cleaning solution injection tube into each channel and a switching operation of the valve of each channel. Procedures for cleaning the channels of an endoscope have therefore been complex. With the conventional system as described above, there is an important problem in that incomplete cleaning frequently occurs, especially the small portions of the valve body or the portion of the cylinder which is covered by the valve body.

In view of this problem, the present applicant has proposed, in Japanese Patent Disclosure No. 58-15836 published on Jan. 29, 1983, a cleaning instrument for cleaning the channels of an endoscope which is free from such a problem. According to this instrument, the cleaning solution is supplied through an air/liquid supply cylinder and a suction cylinder placed in the control section of an endoscope so as to simultaneously clean the interiors of the channels and the inner surfaces of the cylinders. More specifically, valve bodies inserted in the air/liquid supply cylinder and suction cylinder are pulled out, and adaptors are inserted in the open cylinders. Liquid supply tubes connected to these adaptors are connected to a liquid supply pump. A liquid is supplied from the liquid supply pump to the respective cylinders. The liquid then flows from the cylinders to the suction opening and nozzle provided at the distal end of the endoscope and to the air supply port, liquid supply port, and suction port of the connector through the liquid supply channel, the air supply channel, and suction channel of the endoscope.

However, the various channels of an endoscope generally have different inner diameters. More specifically, the air supply channel and liquid supply channel generally have small diameters while the suction channel has a large diameter. With one single channel alone, that portion of the channel which extends in the insertion section of the endoscope has a small diameter, and that portion of the channel which extends in the light guide cable has a large diameter. For this reason, when a liquid is supplied from the cylinders to the respective channels, the liquid flows to the channel or channel portion offering the least flow resistance, and a sufficient amount of cleaning solution cannot flow to a channel or channel portion offering a larger flow resistance. This results in a problem of incomplete cleaning of the endoscope channels.

SUMMARY OF THE INVENTION

Accordingly, the object of the present invention is to provide a method of cleaning an endoscope, which makes it possible to easily and completely clean the channels and valve cylinders of an endoscope.

According to an aspect of the invention there is provided a method of cleaning an endoscope, which comprises a first step of closing the open end of an air/liquid supply valve cylinder; a second step of bringing one end of an air supply channel and one end of a liquid supply channel into contact with a liquid; and a third step of sucking the liquid from a nozzle communicating with the other ends of the air supply channel and liquid supply channel through the two channels and the air/liquid supply valve cylinder, thereby cleaning the interiors of these channels and the cylinder.

DETAILED DESCRIPTION OF THE PREFERRED EMBODIMENT

A few preferred embodiments of the present invention will now be described with reference to the accompanying drawings.

Figure 1:
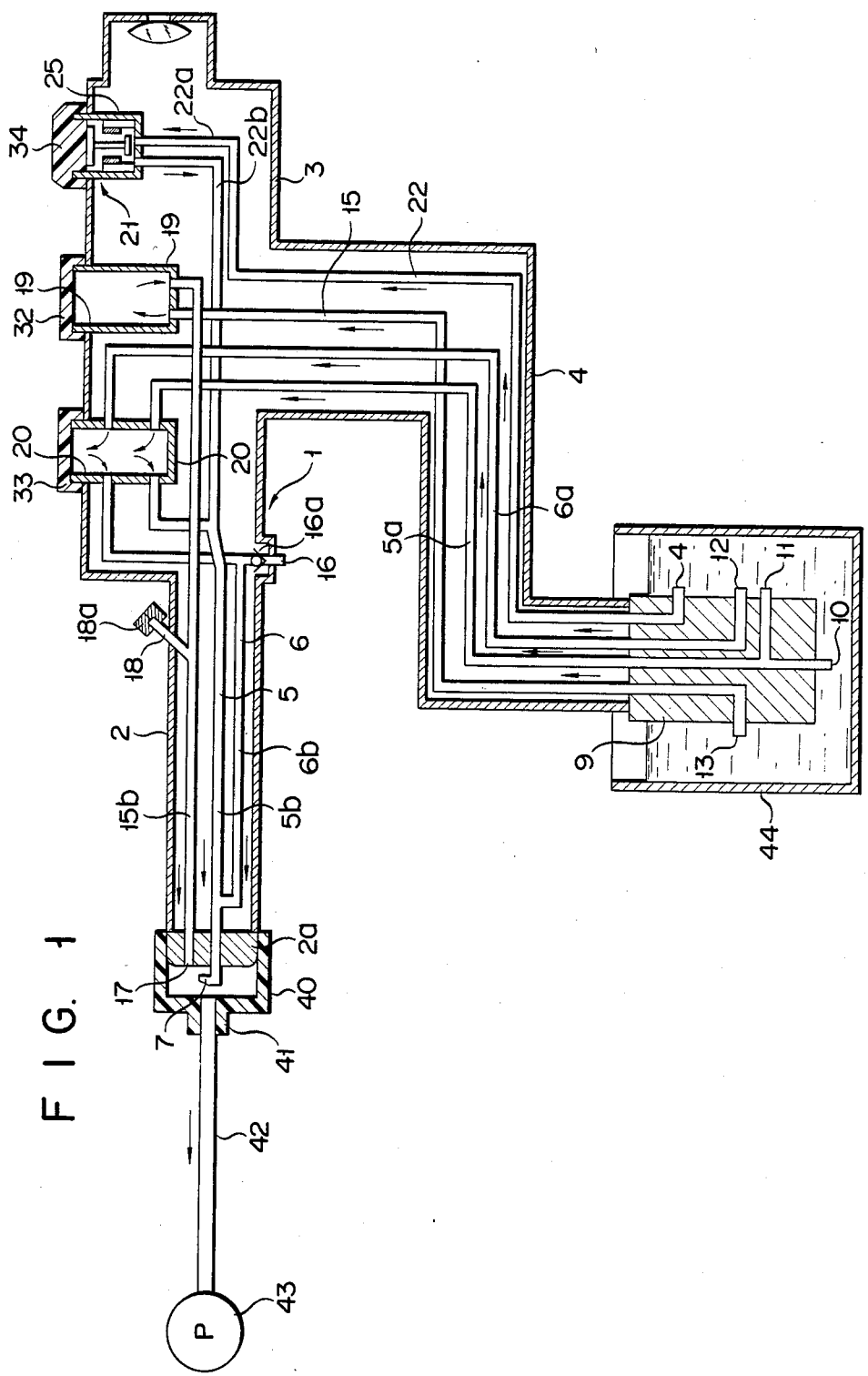
FIG. 1 is a sectional view of an endoscope, illustrating how to clean the endoscope by a first method according to the invention.

FIG. 1 is a sectional view of an endoscope 1. The endoscope 1 comprises a control section 3, an insertion section 2 extending from the control section 3, and a light guide cable 4 extending from the control section 3. Various channels (described later) are formed inside the endoscope 1. An air supply channel 5 and a liquid supply channel 6 extend through the insertion section 2, the control section 3, and the light guide cable 4. The distal ends of these channels 5, 6 are connected to an air/liquid supply nozzle 7 provided at the distal end 2a of the insertion section 2. The nozzle 7 is arranged to face the outer surface of an observation window (not shown) so as to spray air or a liquid to the window. The light guide cable 4 has a connector 9 at the free end. The connector 9 has first and second air supply ports 10 and 11 both communicating with the air supply channel 5, a liquid supply port 12 communicating with the liquid supply channel 6, a suction port 13 communicating with a suction channel to be described later, and a gas supply port 14. When the connector 9 is connected to a light source device (not shown), the first air supply port 10 is connected to an air supply pump in the light source device. The second air supply port 11 and the liquid supply port 12 are connected to a liquid supply tank (not shown). The suction port 13 is connected to a suction pump 13b as a vacuum suction unit through a suction tube 13a.

A suction channel 15 extends along the entire length of the insertion section 2, the control section 3, and the light guide cable 4. That end portion of the suction channel 15, which is at the side of the insertion section 2, serves as an instrument insertion channel 15b. The distal end of the instrument insertion channel 15b communicates with a suction opening 17 opening to the distal end face of the insertion section 2. The proximal end of the instrument insertion channel 15b opens externally at the control section 3 to form a forceps port 18. The forceps port 18 is closed with a detachable stop 18a. A sub liquid supply port 16 having a check valve 16a communicates with the liquid supply channel 6.

Figure 2:
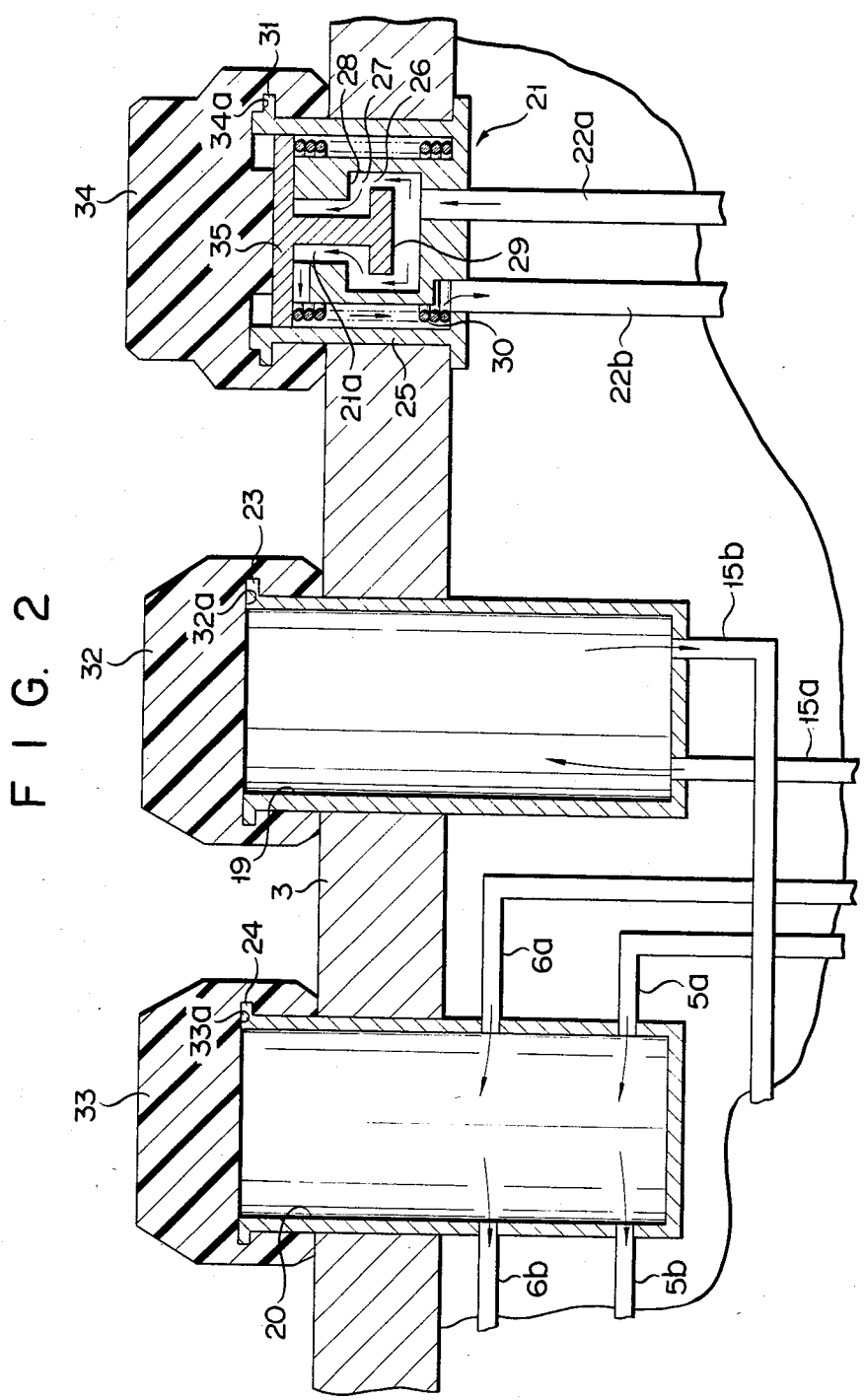
FIG. 2 is an enlarged sectional view of the control section of the endoscope shown in FIG. 1.

The instrument insertion channel 15b is connected to the proximal end of the remaining portion of the suction channel 15 through a suction cylinder, that is, a suction valve cylinder 19. An air/liquid supply cylinder or air/liquid supply valve cylinder 20 is inserted midway along both the air supply channel 5 and the liquid supply channel 6. The valve cylinders 19 and 20 are arranged next to each other at a side surface of the control section 3. The upper ends of the valve cylinders 19 and 20 open to the outside of the control section 3. A gas supply valve 21 is arranged next to the cylinder 19. A channel 22 is connected to the gas supply valve 21. One end of the channel 22 is connected to the air supply channel 5 at a position between the air/liquid supply valve cylinder 20 and the nozzle 7. The other end of the gas supply channel 22 is connected to the gas supply port 14. The valve cylinders 19 and 20 and the gas supply valve 21 have the construction shown in FIG. 2. The suction valve cylinder 19 has a bottom and a flange 23 formed integrally at its open edge or upper edge. The air/liquid supply valve cylinder 20 similarly has a bottom and a flange 24 formed integrally at its open edge. The gas supply valve 21 includes a cylinder 25 and a valve mechanism 26 mounted therein. A valve chamber 27 is formed concentrically in the cylinder 25. A valve body 29, which may be brought into contact with a valve seat 28, is arranged inside the valve chamber 27. The valve body 29 is normally biased by a coil spring 30 to be in contact with the valve seat 28, that is, biased in the valve closing direction. Thus, the valve body 29 normally provides a seal in a path 21a connecting an upstream portion 22a and a downstream channel portion 22b of the gas supply channel 22. A flange 31 is formed integrally with the open end of the cylinder 25. Stops 32 and 33 are attached to the cylinders 19 and 20, respectively, to close their open ends. Engagement grooves 32a and 33a, engaging with the flanges 23 and 24, are formed in the inner surfaces of the stops 32 and 33, so as to prevent the stops from being inadvertently removed even if the pressure rises in the cylinders 19 and 20. A stop 34 is mounted in the cylinder 25 of the gas supply valve 21 to close its open end. A projection 35 projects downward from the center of the stop 34. When the stop 34 is mounted on the cylinder 25, the projection 35 presses the valve body 29 against the biasing force of the coil spring 30, so that the valve body 29 is separated from the valve seat 28 to open the path 21a. An engagement groove 34a is formed in the stop 34 for engagement with the flange 31a for a similar purpose as described above.

Pistons (not shown) are generally inserted in the valve cylinders 19, 20, and 25. These pistons allow or block the communication between the upstream portions 5a, 6a, 15a, and 22a of the channels 5, 6, 15, and 22, on the one hand, and the downstream portions 5b, 6b, 15b, and 22b thereof, on the other hand. However, when the stops 32, 33, 34 are to be mounted on the cylinders 19, 20, and 25, respectively, the pistons are removed first.

The method of cleaning the endoscope 1, which has been described above, will now be explained in greater detail. First, the pistons are removed from the cylinders 19, 20, and 25. As shown in FIG. 1, the stops 32, 33, and 34 are then attached to the cylinders. A detachable cap 40 is airtightly mounted on the distal end 2a of the insertion section. The cap 40 has a connecting portion 41. A suction tube 42 is connected at one end to this portion 41. The other end of the tube 42 is connected to the suction side of a suction pump 43. The delivery side of the pump is connected to a liquid tank (not shown) by a discharge tube (not shown, either). The connector 9 is submerged in liquid L held in the liquid tank 44.

When the pump 43 is operated under this condition, the interiors of the downstream portions 5b, 6b, 15b of the channels 5, 6, 15, which communicate with the nozzle 7 and suction opening 17, are kept at a negative pressure. The interiors of the upstream portions 5b and 6b, which communicate with the downstream portions 5a and 6a via the cylinder 20, are also kept at a negative pressure. The interior of the upstream portion 22a, which communicates with the downstream portion 5b and also with the downstream portion 22b via the cylinder 25, is also kept at a negative pressure. The interior of the upstream portion 15a, which communicates with the downstream portion 15b through the cylinder 19, is also kept at a negative pressure.

As long as the interiors of the channels 5, 6, 15, and 22 and cylinders 19, 20, and 25 are kept at a negative pressure, the liquid L is sucked into the channels 5, 6, 15, and 20. The liquid L flows into the upstream portion 5a of the air supply channel 5 via the first and second air supply ports 10, 11. It further flows into the upstream portion 6a of the liquid supply channel 6 via the liquid supply port 12. At the same time, it flows into the upstream protions 15a and 22a through the suction port 13 and gas supply port 14. In the meantime, the liquid L flows from the upstream portions 5a and 6a into the valve cylinder 20 and then flows into the cap 40 through the downstream portions 5b and 6b and through the nozzle 7. Finally, it is sucked into the pump 43 through the suction tube 42. It also enters the suction valve cylinder 19, flows into the cap 40 via the downstream portion 15b and suction opening 17, and is sucked into the pump 43 via the suction tube 42. On the other hand, the liquid L, which has flown to the upstream portion 22a, flows into the cylinder 25 and further flows as indicated by the arrows shown in FIG. 2. Then, it flows from the cylinder 25 into the cap 40 through the downstream portion 22b and nozzle 7, and is sucked into the pump 43 via the tube 42.

As the liquid L flows as described above, the interiors of the channels 5, 6, 15, and 22 are cleaned. At the same time, the interiors of the cylinders 19, 20 and 25 are also cleaned. Since the liquid L flows outward from the nozzle 7 and suction opening 17, the contaminants can be completely removed from the nozzle and suction opening.

In the above description, the liquid is water or a disinfectant. Hence, the word "cleaning" means both water-washing and disinfection.

According to the first embodiment, the channels and cylinders of an endoscope can be easily and satisfactorily cleaned. Since the liquid is drawn in by vacuum suction, it completely fills the channels, irrespective of the different inner diameters of the channels and cylinders. This ensures proper cleaning. The method also provides excellent operability since it requires no special operations.

In the first embodiment, only the connector 9 is dipped in the liquid L. Instead, the entire endoscope 1 may be submerged in the liquid so that the outer surface of the endoscope can be cleaned at the same time the channels 5, 6, 15, and 22 are cleaned.

Figure 3:
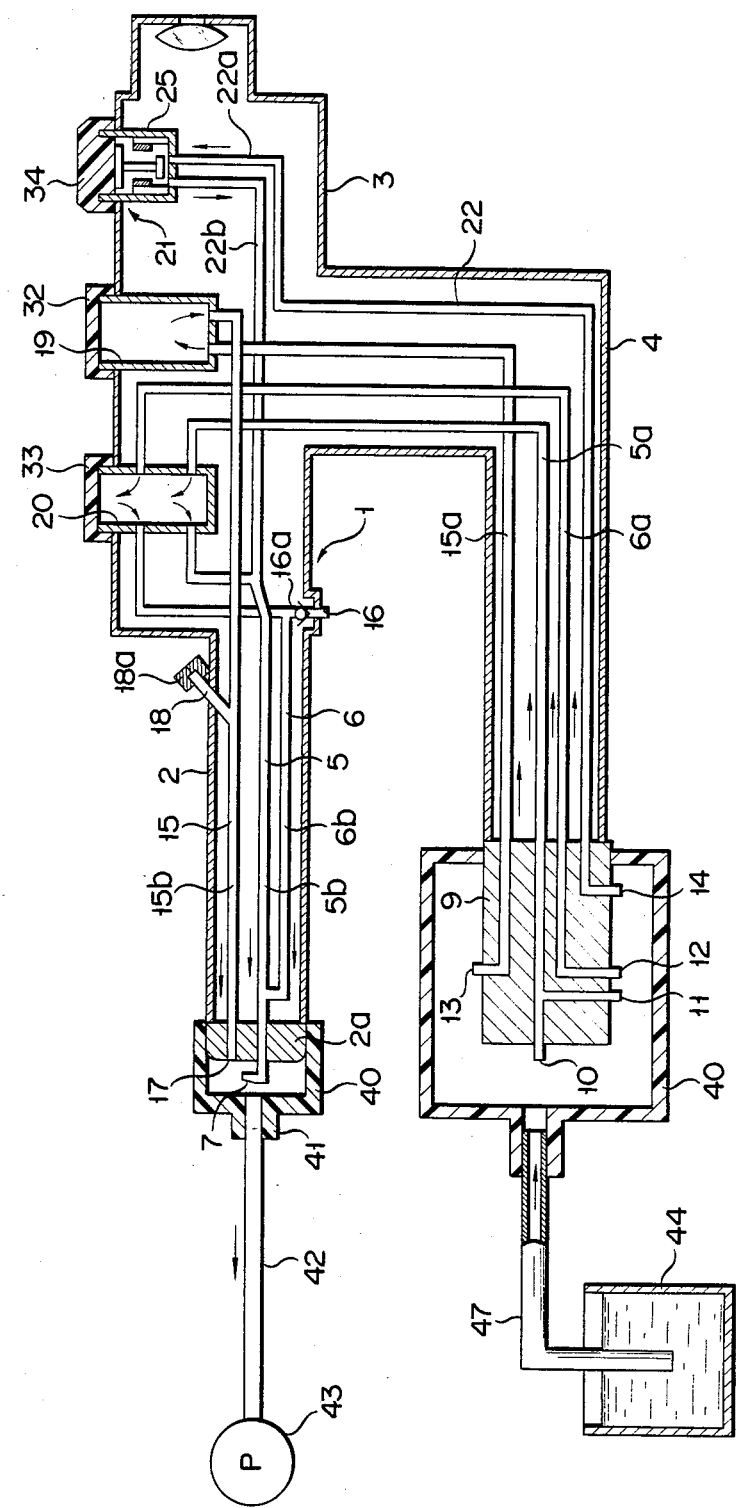
FIG. 3 is an sectional view of the endoscope, showing how to clean the endoscope by a second method according to the invention.

FIG. 3 shows how to clean the endoscope 1 by another method according to the invention. In this embodiment, instead of the connector 9, one end of the liquid supply tube 47 may be submerged in the liquid L, which is connected at the other end to a hollow cylindrical cover 46 mounted on the connector 9. In the second embodiment, the channels 5, 6, 15, and 22 and the cylinders 19, 20, and 25 can be cleaned exactly in the same way as in the first embodiment.

Although the first and second embodiments are used to clean an endoscope which has a gas supply valve and a gas supply channel, among other things, the present invention can be similarly applied to an endoscope which has neither a gas supply valve nor a gas supply channel. Moreover, the method of the invention may be used to clean an endoscope which does not have a gas supply valve, a gas supply channel, a suction valve cylinder or a suction channel. Further, the present invention can be applied to an endoscope in which an air supply channel and a liquid supply channel communicate with two nozzles provided at a distal end of the insertion section of the endoscope. The means for sucking liquid is not limited to a suction pump; it may be a piston-type syringe, for instance.

What is claimed is:

1. A method of cleaning an endoscope which includes a control section, an insertion section extending from the control section and having a nozzle at its distal end, a light guide cable extending from the control section and having a connector at its distal end, an air supply channel extending in the endoscope and having one end communicating with the nozzle and the other end opening to the connector, a liquid supply channel extending in the endoscope and having one end communicating with the nozzle and the other end opening to the connector, a suction channel extending in the endoscope and having one end opening to the distal end of the insertion section and the other end opening to the connector, an air/liquid supply valve cylinder arranged in the control section to communicate with the air supply channel and liquid supply channel and having one end opening to the outside of the control section, and a suction valve cylinder arranged in the control section to communicate with the suction channel and having one end opening to the outside of the control section;

said method comprising the steps of:

closing the open ends of the air/liquid supply valve cylinder and the suction valve cylinder;

causing said other ends of the air supply channel, liquid supply channel and the suction channel to contact with a liquid;

mounting a cap on the distal end of the insertion section so that the nozzle and said one end of the suction channel open to the interior of the cap and connecting the cap to sucking means; and sucking the liquid through the cap from the nozzle and said one end of the suction channel through the three channels, the air/liquid supply valve cylinder and suction valve cylinder, thereby cleaning the interiors of these channels and valve cylinders with the liquid.

2. A method according to claim 1, wherein said contact with said liquid includes submerging the connector in the liquid.

3. A method according to claim 1, wherein said endoscope includes a gas supply channel extending in the endoscope and having one end communicating with the air supply channel at a position between the nozzle and the air/liquid supply valve cylinder and the other end opening to the collector, and a gas supply valve cylinder arranged in the control section to communicate with the gas supply channel and having one end opening to the outside of the control section; said closing step including closing the open end of the gas supply valve cylinder; said contact with said liquid including bringing said other end of the gas supply channel into contact with said liquid; and said sucking step including sucking the liquid from the nozzle and said one end of the suction channel through the four channels and the three valve cylinders, thereby cleaning the interiors of these channels and valve cylinders with the liquid.

* * * * *